(12) United States Patent
Ringeisen et al.

(10) Patent No.: US 6,905,738 B2
(45) Date of Patent: *Jun. 14, 2005

(54) GENERATION OF VIABLE CELL ACTIVE BIOMATERIAL PATTERNS BY LASER TRANSFER

(75) Inventors: Bradley R. Ringeisen, Alexandria, VA (US); Douglas B. Chrisey, Bowie, MD (US); Alberto Pique, Crofton, MD (US); R. Andrew McGill, Lorton, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 79 days.

This patent is subject to a terminal disclaimer.

(21) Appl. No.: 10/068,315
(22) Filed: Feb. 8, 2002
(65) Prior Publication Data

US 2002/0122898 A1 Sep. 5, 2002

Related U.S. Application Data

(60) Continuation-in-part of application No. 09/671,166, filed on Sep. 28, 2000, now Pat. No. 6,766,764, which is a division of application No. 09/318,134, filed on May 25, 1999, now Pat. No. 6,177,151.
(60) Provisional application No. 60/269,384, filed on Feb. 20, 2001, and provisional application No. 60/117,468, filed on Jan. 27, 1999.

(51) Int. Cl.$^7$ .................. C23C 14/30; C23C 14/28; B05D 3/00
(52) U.S. Cl. .................. 427/596; 427/595; 427/554; 427/555
(58) Field of Search .................. 427/554, 555, 427/595, 596, 597, 582, 583, 584, 553, 556

(56) References Cited

U.S. PATENT DOCUMENTS 3,745,586 A   7/1973   Braudy (Continued)

FOREIGN PATENT DOCUMENTS

DE   2113336   9/1971

OTHER PUBLICATIONS

Tolbert et al, "Laser Ablation Transfer Imaging Using Picosecond Optical Pulses: Ultra–High Speed, Lower Threshold and High Resolution" Journal of Imaging Science and Technology, vol. 37 No. 5 Sep./Oct. 1993 pp. 485–489.

(Continued)

*Primary Examiner*—Shrive P. Beck
*Assistant Examiner*—Eric B Fuller
(74) *Attorney, Agent, or Firm*—John J. Karasek; Joseph T. Grunkemeyer

(57) ABSTRACT

A method for depositing a transfer material onto a receiving substrate uses a source of laser energy, a receiving substrate, and a target substrate. The target substrate comprises a laser-transparent support having a laser-facing surface and a support surface. The target substrate also comprises a composite material having a back surface in contact with the support surface and a front surface. The composite material comprises a mixture of the transfer material to be deposited and a matrix material. The matrix material is a material that has the property that, when it is exposed to laser energy, it desorbs from the laser-transparent support. The source of laser energy is positioned in relation to the target substrate so that laser energy is directed through the laser-facing surface of the target substrate and through the laser-transparent support to strike the composite material at a defined target location. The receiving substrate is positioned in a spaced relation to the target substrate. The source of laser energy has sufficient energy to desorb the composite material at the defined target location, causing the composite material to desorb from the defined target location and be lifted from the support surface of the laser-transparent support. The composite material is deposited at a defined receiving location on the receiving substrate. The method is useful for creating a pattern of biomaterial on the receiving substrate.

50 Claims, 2 Drawing Sheets

U.S. PATENT DOCUMENTS

| | | | |
|---|---|---|---|
| 3,978,247 A | | 8/1976 | Braudy et al. |
| 4,064,205 A | | 12/1977 | Landsman |
| 4,245,003 A | | 1/1981 | Oransky et al. |
| 4,702,958 A | | 10/1987 | Itoh et al. |
| 4,752,455 A | | 6/1988 | Mayer |
| 4,895,735 A | | 1/1990 | Cook |
| 4,970,196 A | | 11/1990 | Kim et al. |
| 4,987,006 A | * | 1/1991 | Williams et al. ............ 427/597 |
| 5,156,938 A | | 10/1992 | Foley et al. |
| 5,171,650 A | | 12/1992 | Ellis et al. |
| 5,173,441 A | | 12/1992 | Yu et al. |
| 5,256,506 A | | 10/1993 | Ellis et al. |
| 5,292,559 A | * | 3/1994 | Joyce et al. ................ 427/597 |
| 5,308,737 A | * | 5/1994 | Bills et al. .................. 430/201 |
| 5,492,861 A | | 2/1996 | Opower |
| 5,567,336 A | | 10/1996 | Tatah |
| 5,582,752 A | | 12/1996 | Zair |
| 5,725,706 A | | 3/1998 | Thoma et al. |
| 5,725,914 A | | 3/1998 | Opower |
| 5,736,464 A | | 4/1998 | Opower |
| 5,741,560 A | * | 4/1998 | Ross .......................... 427/555 |
| 6,025,036 A | | 2/2000 | McGill et al. |
| 6,040,139 A | | 3/2000 | Bova |
| 6,056,907 A | | 5/2000 | Everett et al. |
| 6,159,832 A | * | 12/2000 | Mayer ........................ 438/584 |
| 6,165,170 A | | 12/2000 | Wynne |
| 6,177,151 B1 | * | 1/2001 | Chrisey et al. ............. 427/596 |
| 6,495,195 B2 | * | 12/2002 | Baer et al. .................. 427/2.11 |

OTHER PUBLICATIONS

Adrian et al, "A Study of the Mechanism of Metal Deposition by the Laser–Induced Forward Transfer Process" J. Vac. Sci. Technol. B5 (5), Sep./Oct. 1987 pp. 1490–1494.

Bohandy et al, Metal Deposition from a Supported Metal Film Using an Excimer Laser, J. Appl. Phys. 60 (4) Aug. 15, 1986 pp. 1538–1539.

von Gutfeld, R., Enhancing Ribbon Transfer Using Laser Printing, IBM Technical Disclosure Bulletin, vol. 17, No. 6, Nov., 1974.

McGill, et al., "Choosing Polymer Coatings for Chemical Sensors", CHEMTECH Journal, American Chemical Society, vol. 24, No. 9, Sep. 1994 pp. 27–37.

Ringeisen et al, "Generation of Mesoscopic Patterns of Viable *Escherichia Coli* by Ambient Laser Transfer", Biomaterials, vol. 23, 2002 pp. 161–166.

Wu et al, "The Deposition, Structure, Pattern Deposition, and Activity of Biomaterial Thin–Films by Matrix–Assisted Pulsed–Laser Evaporation (MAPLE) and MAPLE Direct Write", Thin Solid Films, vol. 398–399, 2002 pp. 607–614

Chrisey et al, "Matrix Assisted Pulsed Laser Evaporation Direct Write", Divisional U.S. Appl. No. 09/671,166, filed Sep. 28, 2000, pp. 1–12.

Ringeisen et al, "Generation of Viable Cell and Active Biomaterial Patterns By Laser Transfer", Provisional U.S. Appl. No. 60/269,384, filed Feb. 20, 2001, pp. 1–54.

Ringeisen et al, "Generation of Biomaterial Microarrays By Laser Transfer", Non–Provisional U.S. Appl. No. 10/068, 364, filed Feb. 8, 2002 pp. 1–34.

Meneghini et al, "Transfer Printing Medium", PCT International Application, PCT/US94/11345, Filed Oct. 6, 1994, pp. 1–22.

Young et al, "Jetting Behavior in the Laser Forward Transfer of Rheological Fluids", Provisional U.S. Appl. No. 60/327, 733, filed Oct. 10, 2001, pp. 1–46.

Auyeung et al, "Laser Forward Transfer of Rheological Systems", Provisional U.S. Appl. No. 60/290,400, filed May 5, 2001, 1–17.

* cited by examiner

GENERATION OF VIABLE CELL ACTIVE BIOMATERIAL PATTERNS BY LASER TRANSFER

This nonprovisional application is a continuation-in-part application of U.S. patent application Ser. No. 09/671,166 filed on Sep. 28, 2000, now U.S. Pat. No. 6,766,764 which is a divisional application of Ser. No. 09/318,134, now U.S. Pat. No. 6,177,151 filed on May 25, 1999, which claims benefit of U.S. provisional patent application 60/117,468 filed on Jan. 27, 1999. This application also claims benefit of U.S. provisional patent application 60/269,384 filed on Feb. 20, 2001 as to certain matter. All applications and patents named above are incorporated herein by reference.

BACKGROUND OF THE INVENTION

1. Field of the Invention

The invention relates generally to a method for the deposition of materials and more specifically to a method for direct writing of a wide range of different biomaterials onto a substrate.

2. Description of the Prior Art

The term "direct write" refers generally to any technique for creating a pattern directly on a substrate, either by adding or removing material from the substrate, without the use of a mask or preexisting form. Direct write technologies have been developed in response to a need in the electronics industry for a means to rapidly prototype passive circuit elements on various substrates, especially in the mesoscopic regime, that is, electronic devices that straddle the size range between conventional microelectronics (sub-micron-range) and traditional surface mount components (10+ mm-range). (Direct writing may also be accomplished in the sub-micron range using electron beams or focused ion beams, but these techniques, because of their small scale, are not appropriate for large-scale rapid prototyping.) Direct writing allows for circuits to be prototyped without iterations in photolithographic mask design and allows the rapid evaluation of the performance of circuits too difficult to accurately model. Further, direct writing allows for the size of printed circuit boards and other structures to be reduced by allowing passive circuit elements to be conformably incorporated into the structure. Direct writing methods for transferring electronic materials can also be useful for transferring biomaterials to make simple or complex biomaterial structures, with or without associated electronic circuitry. Direct writing can be controlled with CAD/CAM programs, thereby allowing electronic circuits to be fabricated by machinery operated by unskilled personnel or allowing designers to move quickly from a design to a working prototype. Mesoscopic direct write technologies have the potential to enable new capabilities to produce next generation applications in the mesoscopic regime.

Currently known direct write technologies for adding materials to a substrate include ink jet printing, Micropen® laser chemical vapor deposition (LCVD), laser particle guidance (Optomec, Inc.), and laser engineered nano-shaping (LENS). Currently known direct write technologies for removing material from a substrate include laser machining, laser trimming and laser drilling.

The direct writing techniques of ink jet printing, screening, and Micropen® are wet techniques, that is, the material to be deposited is combined with a solvent or binder and is squirted onto a substrate. The solvent or binder must later be removed by a drying or curing process, which limits the flexibility and capability of these approaches. In addition, wet techniques are inherently limited by viscoelastic properties of the fluid in which the particles are suspended or dissolved.

In the direct writing technique known as "laser induced forward transfer" (LIFT), a pulsed laser beam is directed through a laser-transparent target substrate to strike a film of material coated on the opposite side of the target substrate. The laser vaporizes the film material as it absorbs the laser radiation and, due to the transfer of momentum, the material is removed from the target substrate and is redeposited on a receiving substrate that is placed in proximity to the target substrate. Laser induced forward transfer is typically used to transfer opaque thin films, typically metals, from a pre-coated laser transparent support, typically glass, $SiO_2$, $Al_2O_3$, $SrTiO_3$, etc., to the receiving substrate. Various methods of laser-induced forward transfer are described in, for example, the following U.S. patents and publications incorporated herein by reference: U.S. Pat. No. 4,752,455 to Mayer, U.S. Pat. No. 4,895,735 to Cook, U.S. Pat. No. 5,725,706 to Thoma et al., U.S. Pat. No. 5,292,559 to Joyce, Jr. et al., U.S. Pat. No. 5,492,861 to Opower, U.S. Pat. No. 5,725,914 to Opower, U.S. Pat. No. 5,736,464 to Opower, U.S. Pat. No. 4,970,196 to Kim et al., U.S. Pat. No. 5,173,441 to Yu et al., and Bohandy et al., "Metal Deposition from a Supported Metal Film Using an Excimer Laser, J. Appl. Phys. 60 (4) Aug. 15, 1986, pp 1538–1539. Because the film material is vaporized by the action of the laser, laser induced forward transfer is inherently a homogeneous, pyrolytic technique and typically cannot be used to deposit complex crystalline, multi-component materials or materials that have a crystallization temperature well above room temperature because the resulting deposited material will be a weakly adherent amorphous coating. Moreover, because the material to be transferred is vaporized, it becomes more reactive and can more easily become degraded, oxidized, or contaminated. The method is not well suited for the transfer of organic materials, since many organic materials are fragile, thermally labile, and can be irreversibly damaged during deposition. Moreover, functional groups on an organic polymer can be irreversibly damaged by direct exposure to laser energy. Neither is the method well suited for the transfer of biomaterials. The cells or biomolecules can be damaged during deposition. Other disadvantages of the laser induced forward transfer technique include poor uniformity, morphology, adhesion, and resolution. Further, because of the high temperatures involved in the process, there is a danger of ablation or sputtering of the support, which can cause the incorporation of impurities in the material that is deposited on the receiving substrate. Another disadvantage of laser induced forward transfer is that it typically requires that the coating of the material to be transferred be a thin coating, generally less that 1 $\mu$m thick. Because of this requirement, it is very time-consuming to transfer more than very small amounts of material.

In a simple variation of the laser induced forward deposition technique, the target substrate is coated with several layers of materials. The outermost layer, that is, the layer closest to the receiving substrate, consists of the material to be deposited and the innermost layer consists of a material that absorbs laser energy and becomes vaporized, causing the outermost layer to be propelled against the receiving substrate. Variations of this technique are described in, for example, the following U.S. patents and publications incorporated herein by reference: U.S. Pat. No. 5,171,650 to Ellis et al., U.S. Pat. No. 5,256,506 to Ellis et al., U.S. Pat. No. 4,987,006 to Williams et al., U.S. Pat. No. 5,156,938 to Foley et al. and Tolbert et al., "Laser Ablation Transfer Imaging Using Picosecond Optical pulses: Ultra-High Speed, Lower Threshold and High Resolution" Journal of imaging Science and Technology, Vol. 37, No. 5, September/October 1993 pp. 485–489. A disadvantage of this method is that, because of the multiple layers, it is difficult or impossible to achieve the high degree of homogeneity of deposited material on the receiving substrate required, for example, for the construction of electronic devices, sensing devices or passivation coatings.

U.S. Pat. No. 6,177,151 to Chrisey et al. discloses the MAPLE-DW (Matrix Assisted Pulsed Laser Evaporation Direct Write) method and apparatus. The method comprises the use of laser energy to cause a composite material to volatilize, desorb from a laser-transparent support, and be deposited on a receiving substrate. The composite material comprises a matrix material and a transfer material. The transfer material is the material desired to be transferred to the receiving substrate. The matrix material is more volatile than the transfer material and binds the transfer material into the composite material. The laser energy causes the matrix material to volatilize and propel the transfer material onto the receiving substrate. The properties of the transfer material are preserved after deposition. This method will be further described in the Detailed Description of the Preferred Embodiments below.

U.S. Pat. No. 6,177,151 is primarily directed to the transfer of electronic materials to form circuitry on the receiving substrate. It also discloses the transfer of chemoselective materials and bioselective materials. Examples of biochemical materials disclosed include proteins, oligopeptides, polypeptides, whole cells, biological tissue, enzymes, cofactors, nucleic acids, DNA, RNA, antibodies (intact primary, polyclonal, and monoclonal), antigens, oligosaccharides, polysaccharides, oligonucleotides, lectins, biotin, streptavidin, and lipids. The prior art does not disclose MAPLE-DW transfer of living or active biomaterials.

There is need for a method for transferring living or active biomaterials in such a way that desired properties of the biomaterials are preserved. The biomaterials should remain living or active after deposition onto the receiving substrate. Such a method would be useful to generate micron-scale patterns of living cells and active biomaterials for next generation 3-D tissue engineering, fabrication of cell, protein, or antibody-based microfluidic biosensor arrays, and selective separation and culturing of microorganisms. There is also a need for a method to micromachine away portions of a receiving substrate and or deposited transfer material using the same laser-transfer apparatus.

SUMMARY OF THE INVENTION

It is an object of the invention to provide methods for depositing a transfer material on a receiving substrate wherein a pattern of deposited composite material can be created directly on the receiving substrate without the use of a mask.

It is a further object of the invention to provide a method that is useful for depositing a wide range of transfer materials including living or active biomaterials with no damage to the transfer material.

It is a further object of the invention to provide a method for depositing a transfer material on a receiving substrate at ambient conditions.

It is a further object of the present invention to provide a method for depositing a transfer material on a receiving substrate by laser induced deposition wherein the spatial resolution of the deposited composite material can be as small as 1 $\mu$m.

It is a further object of the invention to provide a method for depositing transfer materials on a receiving substrate in a controlled manner wherein the process can be computer-controlled.

It is a further object of the invention to provide a method for depositing transfer materials on a receiving substrate in a controlled manner wherein it is possible to switch rapidly between different transfer materials to be deposited on the receiving substrate.

It is a further object of the invention to provide a method to micromachine away a portion of a receiving substrate or deposited composite material.

These and other objects of the invention are accomplished by a method for laser deposition comprising the steps of: providing one or more sources of laser energy that produce laser energy; providing a receiving substrate; wherein the receiving substrate is positioned opposite the source of laser energy; providing a target substrate; wherein the target substrate is positioned between the receiving substrate and the source of laser energy; wherein the target substrate comprises a laser-transparent support and a composite material; wherein the laser-transparent support has a laser-facing surface facing the source of laser energy; wherein the laser-transparent support has a support surface facing the receiving substrate; wherein the composite material has a back surface in contact with the support surface; wherein the composite material has a front surface facing the receiving substrate; wherein the composite material comprises a matrix material and a transfer material; and wherein the matrix material has the property of being desorbed from the laser-transparent support when exposed to the laser energy; positioning the source of laser energy in a spaced relation to the target substrate so that the laser energy will strike the composite material at a defined target location; positioning the receiving substrate in a spaced relation to the target substrate; and exposing the target substrate to the laser energy; wherein the laser energy is directed through the laser-facing surface and through the laser-transparent support to strike the composite material at the support surface-back surface interface at a defined target location; wherein the laser energy has sufficient energy to cause the desorption of the composite material from the support surface; and wherein the desorbed composite material is deposited at a defined receiving location on the receiving substrate to form a deposited composite material.

LIST OF REFERENCE NUMBERS

| | |
|---|---|
| 12 | source of laser energy |
| 14 | laser energy |
| 15 | laser-transparent support |
| 16 | composite material |
| 17 | target substrate |
| 18 | receiving substrate |
| 19 | laser-absorbing layer |
| 20 | laser positioning means |
| 22 | target substrate positioning means |
| 24 | receiving substrate positioning means |
| 26 | deposited composite material |
| 28 | defined machining location |
| 30 | laser-facing surface |
| 32 | support surface |
| 34 | back surface |
| 36 | front surface |

DETAILED DESCRIPTION OF THE PREFERRED EMBODIMENTS

Figure 1A:
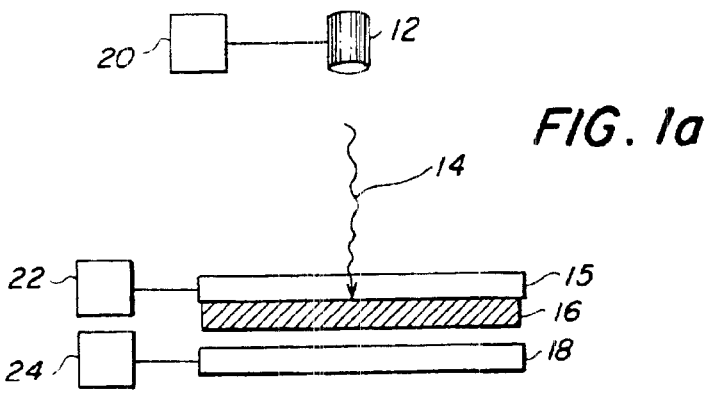
FIG. 1*a* is a schematic representation of a MAPLE-DW apparatus when used to transfer composite material 16 to a receiving substrate 18.
Figure 4:
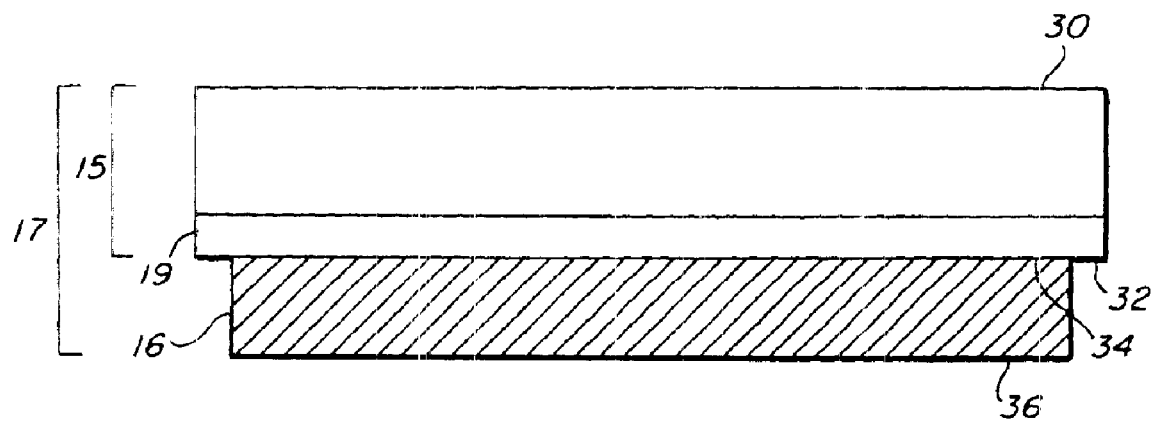
FIG. 4 is a detailed schematic representation of a target substrate 17 with a laser-absorbing layer 19, also showing the laser-transparent support 15, composite material 16, laser-facing surface 30, support surface 32, back surface 34, and front surface 34.

FIG. 1a schematically illustrates a MAPLE-DW apparatus used in the present invention. The apparatus includes a source of laser energy 12 that produces laser energy 14, a target substrate 17, and a receiving substrate 18. The receiving substrate 18 is positioned opposite the source of laser energy 12. The target substrate 17 is positioned between the receiving substrate 18 and the source of laser energy 12. FIG. 4 schematically illustrates the target substrate in detail. The target substrate 17 comprises two layers: a laser-transparent support 15 and a composite material 16. The laser-transparent support 15 has a laser-facing surface 30 that faces the source of laser energy 12 and a support surface 32 that faces the receiving substrate 18. The composite material 16 has a back surface 34 in contact with the support surface 32 and a front surface 36 facing the receiving substrate 18. The composite material 16 comprises a matrix material and a transfer material. The matrix material has the property of being desorbed from the laser-transparent support 15 when exposed to the laser energy 14.

The method of the invention for laser deposition comprises the steps of: providing one or more sources of laser energy 12 that produce laser energy 14, providing a receiving substrate 18, providing a target substrate 17, positioning the source of laser energy 12, positioning the receiving substrate 18, and exposing the target substrate 17. In the step of positioning the source of laser energy 12, the source of laser energy 12 is positioned in a spaced relation to the target substrate 17 so that the laser energy 14 will strike the composite material 16 at a defined target location. In the step of positioning the receiving substrate, the receiving substrate 18 is positioned in a spaced relation to the target substrate 17. In the step of exposing the target substrate 17, laser energy 14 from the source of laser energy 12 is directed through the laser-facing surface 30 and through the laser-transparent support 15 to strike the composite material 16 at the support surface-back surface 32, 34 interface at a defined target location. The laser energy 14 has sufficient energy to cause the desorption of the composite material 16 from the support surface 32. The desorbed composite material is deposited at a defined receiving location on the receiving substrate 18 to form a deposited composite material 26. Unless otherwise stated, all steps can be performed in any sequence that results in a deposited composite material 26 on the receiving substrate 18. Preferably, the method is controlled by a computer.

Preferable, the method is carried out at about room temperature and about atmospheric pressure. The method can also be carried out under one or more controlled conditions selected from the group consisting of humidity, atmospheric composition, air pressure, temperature, and sterility.

Figure 2A:
FIGS. 2*a* and 2*b* are schematic representations of the laser-transparent support 15, the composite material 16, and the receiving substrate 18 before (2*a*) and after (2*b*) the depositing of the composite material 16 on the receiving substrate 18 to form a deposited composite material 26.
Figure 2B:
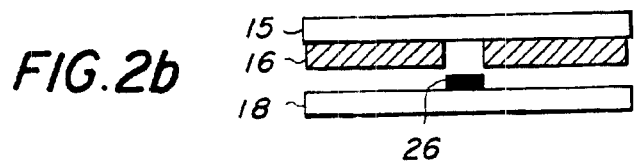

FIGS. 2a and 2b schematically illustrate the effects of exposing the composite material 16 to the laser energy 14, whereby the composite material 16 desorbs from the surface of the target substrate 17 so that the composite material 16 is deposited onto the receiving substrate 18 forming the deposited composite material 26.

Any suitable source of laser energy may be used in the present invention. In general, a pulsed laser is preferred. (As used herein, the terms "laser" and "source of laser energy" are used interchangeably to refer to any device that creates a laser beam.) A pulsed laser has the advantage of generating a very short burst of laser energy 14 that prevents damage to the composite material 16. Lasers for use in accordance with the present invention can be any type such as are generally used with other types of laser deposition. Pulsed lasers are commercially available within the full spectral range from UV to IR. Typically, such lasers emit light having a wavelength in the range of about 157 nm–1100 nm, an energy density of about 0.05–10 J/cm$^2$ (typically about 0.1–2.0 J/cm$^2$), a pulsewidth of about $10^{-12}$–$10^{-6}$ second and a pulse repetition frequency of about 0 to greater than 20,000 Hz. In general, energy density (fluence) affects the morphology of the deposited composite material 26; higher energies tend to produce deposited composite material 26 that have larger particles. Examples of suitable lasers include, but are not limited to, pulsed gas lasers such as excimer lasers, i.e. $F_2$ (157 nm), ArF (193 nm), KrF (248 nm). XeCl (308 nm), XeF (351 μm), $CO_2$, nitrogen, metal vapor, etc.; pulsed solid state lasers such as Nd:YAG, Ti:Sapphire, Ruby, diode pumped, semiconductor, etc.; and pulsed dye laser systems. Typically, the particular laser is selected with regard to the energy needed to desorb the composite material 16 from the support surface 32. Some embodiments of the method use a matrix material that comprises water. In those cases, an ArF excimer laser (193 nm) is suitable, because the water will absorb that wavelength of laser energy 14. The energy density should be high enough to desorb the composite material, but not so high that the laser energy 14 damages the transfer material. When the transfer material is a biomaterial, a typical range of energy density is about 50 to about 200 mJ/cm$^2$. However, higher energy densities are sometimes possible.

The dimensions of the laser energy 14 can be controlled by any means known in the art so that only a precisely defined area of the target substrate 17 is exposed to the laser energy 14 and so that only a precisely defined portion of the composite material 16 desorbs. The laser energy 14 can be focussed through an objective to narrow the beam and desorb a smaller portion of composite material 16. This increases the possible resolution of the deposited composite material 26. It is possible to focus the laser energy 14 so that it is small enough to transfer a single cell to the receiving substrate 18 from a composite material 16 containing a cluster of cells. Single cell transfers can also be achieved by using a very dilute concentration of cells in the composite material 16.

The receiving substrate 18 should be positioned so that when the composite material 16 on the laser-transparent support 15 is desorbed, the composite material 16 can be deposited at a defined receiving location on the receiving substrate 18. Also, there should be enough space between the target substrate 17 and the receiving substrate 18 so that volatilized matrix material, or byproducts from laser-induced decomposition of the matrix material, can escape from the space between the target substrate 17 and the receiving substrate 18. Preferably, the receiving substrate 18 is positioned about 10 to about 100 μm from the surface of the composite material 16.

The laser 12, target substrate 17, and the receiving substrate 18 should be moveable with respect to each other so that the composite material 16 can be deposited in a pattern and so that after the composite material 16 desorbs at one defined target location on the target substrate 17, the laser energy 14 can be directed to another defined target location on the target substrate 17 where the composite material 16 has not yet desorbed. For example, to deposit a line of composite material 16 on the receiving substrate 18, the laser 12 is moved with respect to the target substrate 17 and the receiving substrate 18, which may be held stationary with respect to each other. As the laser 12 moves with respect to the substrates, it directs laser energy 14 to a new defined target location on the target substrate 17 where the composite material 16 has not yet desorbed, and causes the composite material 16 to be deposited onto a new defined receiving location on the receiving substrate 18. The successive defined receiving location may overlap to the extent necessary to create a continuous line of deposited composite material 26 on the receiving substrate 18.

To increase the thickness of deposited composite material 26 at a particular defined receiving location, the laser 12 and the receiving substrate 18 are held stationary with respect to each other and the target substrate 17 is moved with respect to the laser 12 and the receiving substrate 18. The laser energy 14 is directed to a new defined target location on the target substrate 17 where the composite material 16 has not yet desorbed. The composite material 16 is deposited onto the same defined receiving location on the receiving substrate 18 in an increasingly thickened deposit. (As used herein, the terms "moving [a] with respect to [b]" or "moving [a] and [b] with respect to each other" mean that either [a] or [b] can be moved to effect a change in their relative position.)

The steps of positioning the source of laser energy 12 and positioning the receiving substrate 18 can be achieved through the use of one or more positioning means selected from the group consisting of a laser positioning means 20, a target substrate positioning means 22, and a receiving substrate positioning means 24. These positioning means can be any positioning means known in the art for supporting a source of laser energy 12, a target substrate 17, and a receiving substrate 18 and moving them in a controlled and defined manner. For example, similar positioning means and moving means for a laser, target and receiving substrate are known in the fields of laser transfer deposition and laser induced forward transfer. The laser 12 may be positioned in any location that provides an optical path between the laser 12 and the target substrate 17 so that sufficient laser energy 14 can be directed to defined target locations on the target substrate 17. It is not always necessary to use all three positioning means. It is only necessary to control the relative positions of the components such that the laser energy 14 strikes the target substrate 17 at the desired defined target location, and the desorbed composite material 16 lands on the receiving substrate 18 at the desired defined receiving location.

Many embodiments of the general method are possible. The composite material can be deposited in a two-dimensional pattern or a three-dimensional pattern of deposited composite material 26. This done by repeating the steps of positioning the source of laser energy, exposing the target substrate 17, and positioning the receiving substrate at successive defined target locations and successive defined receiving locations. This creates multiple instances of deposited composite material 26 that can be positioned in any two-dimensional pattern or three-dimensional pattern desired. A three-dimensional pattern can be created by placing deposited composite material 26 on top of deposited composite material 26 already on the receiving substrate 18.

Figure 1B:
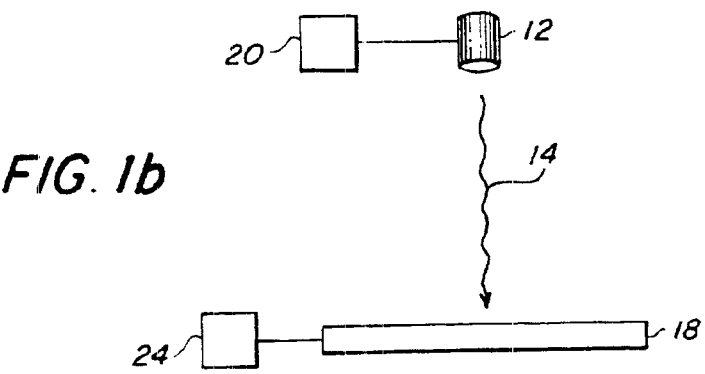
FIG. 1*b* is a schematic representation of the MAPLE-DW apparatus when used to micromachine away a portion of the receiving substrate 18.
Figure 3A:
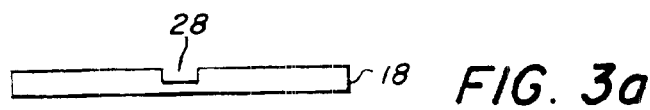
FIGS. 3*a* and 3*b* are schematic representations of a defined machining location 28 on a receiving substrate 18 (3*a*) made using the apparatus of FIG. 1*b*, and a deposited composite material 26 in a defined machining location 28 (3*b*) made using the apparatus of FIG. 1*a*.

The method can also be used to micromachine away portions of the receiving substrate 18. This can be done before the step of providing a target substrate 17 by positioning the receiving substrate 18 in a spaced relation to the source of laser energy 12, and exposing the receiving substrate 18 to the laser energy 14 so that the laser energy 14 machines away a defined machining location 28 on the receiving substrate 18. FIG. 1b schematically illustrates the apparatus used to carry out this method. The laser energy 14 directly strikes the receiving substrate 18 without a target substrate 17 in between. This can be done with the same source of laser energy 12 as is used for desorbing the composite material 16, or a different one. FIG. 3a schematically illustrates the resulting defined machining location 28 on the receiving substrate 18.

Another embodiment can be used to micromachine away portions of the deposited composite material 26 and the receiving substrate 18. This can be done after the steps of exposing the target substrate 17 and positioning the receiving substrate by removing the target substrate 17 from its position between the source of laser energy 12 and the receiving substrate 18, positioning the receiving substrate 18 in a spaced relation to the source of laser energy 12, and exposing the receiving substrate 18 to the laser energy 14 so that the laser energy 14 machines away a defined machining location 28 on the receiving substrate 18 or on the deposited composite material 26. This is essentially the same method as above except that it occurs after the deposited composite material 26 is on the receiving substrate 18.

Figure 3B:

The above micromachining methods can also be used to micromachine a via, or small hole, all the way through the receiving substrate 18. Micromachining is also useful for creating channels in the receiving substrate 18 and for removing excess deposited composite material 26. In another embodiment, the composite material 16 is deposited directly into a defined machining location 28 already micromachined away by the laser energy 14. FIG. 3b schematically illustrates the resulting deposited composite material 26 in a defined machining location 28 on the receiving substrate 18.

In another embodiment the step of providing a target substrate 17 is repeated one or more times using target substrates 17 comprising different composite materials 16. The different composite materials 16 are deposited in respective patterns on the receiving substrate 18. With this method two or more composite materials 16 can be combined on one receiving substrate 18 in any desired combination of patterns. The apparatus of the present invention can be adapted so that a plurality of different composite materials 16 can be deposited consecutively onto a receiving substrate 18 by providing a way to consecutively move each target substrate 17 into a position for depositing material from a particular target substrate 17 onto the receiving substrate 18. Consecutive deposition of different composite materials 16 can also be accomplished by providing a target substrate 17 that is subdivided into a plurality of different subregions that each have a different composite material 16 and providing a way to select a particular subregion and deposit the composite material 16 from that subregion onto the receiving substrate 18. The different composite materials 16 can comprise different transfer materials. This allows the deposition of multi-component structures on the receiving substrate 18.

The laser-transparent support 15 is typically planar, having a support surface 32 that is coated with the composite material 16 and a laser-facing surface 30 that can be positioned so that the laser energy 14 can be directed through the laser-transparent support 15. The composition of the laser-transparent support 15 is selected in accordance with the particular type of laser that is used. For example, if the laser 12 is a pulsed UV laser, the laser-transparent support 15 may be an UV-transparent material including but not limited to quartz or machine etched quartz. If the laser 12 is an IR laser, the laser-transparent support 15 may be an IR-transparent material including, but not limited to plastic, silicon, fused silica, or sapphire. Similarly, if the laser 12 is a visible laser, the laser-transparent support 15 may be a material that is transparent in the visible range, including, but not limited to soda lime and borosilicate glasses. A laser-transparent flexible polymer ribbon can also be a suitable laser-transparent support 15.

The support surface 32 of the laser-transparent support 15 can further comprise a laser-absorbing layer 19 in contact with the back surface 34 of the composite material 16. This is schematically illustrated in FIG. 4. The laser-absorbing layer 19 absorbs the laser energy 14 and vaporizes at the site of absorption. The vaporization aids in the desorption of the composite material 16 from the laser-transparent support 15 and propels the composite material 16 towards the receiving substrate 18. The use of a laser-absorbing layer 19 can result in a cleaner desorption with less damage to the transfer material and a higher resolution. A suitable laser-absorbing layer 19 can comprise one or more materials selected from the group consisting of gold, chrome, and titanium.

The receiving substrate 18 can be any solid material, planar or non-planar, onto which one may wish to deposit the composite material 16. The receiving substrate 18 can comprise one or more materials selected from the group consisting of chemically functionalized glass, polymer-coated glass, quartz, natural hydrogel, synthetic hydrogel, uncoated glass, nitrocellulose coated glass, silicon, glass, plastics, metals, and ceramics. The receiving substrate 18 can comprise functionalization that interacts with the deposited composite material 26. The functionalization is selected from the group consisting of covalent functionalization, physisorbed functionalization, and combinations thereof. Surfaces with functionalization can be prepared by any method known in the art. Surfaces with functionalization can also occur naturally, such as a living host. Covalent functionalization is when the deposited composite material 26 becomes covalently bonded to the surface of the receiving substrate 18. Physisorbed functionalization is when the deposited composite material 26 becomes attached or adsorbed to the receiving substrate 18 by means other than covalent bonding. Examples of functionalization include a living host, a living cell, a living cell culture, a non-living cell, a non-living group of cells, a living tissue, a chemically functionalized surface, and a biologically functionalized surface.

The composite material 16 comprises a matrix material and a transfer material. The transfer material is any functional material of interest to be transferred to the receiving substrate 18 that one may wish to deposit on a substrate in a defined pattern. The purposes of the matrix material are to protect the transfer material from the laser energy and to allow desorption of the composite material 16 from the laser-transparent support 15. The composite material 16 can be a solid, a liquid, or a rheological fluid, although liquids are not preferred.

The transfer material can be any biomaterial. The biomaterial can be in its living or active state. An active biomaterial is one that is capable of performing its natural or intended biological function. Suitable biomaterials can comprise any of the following examples, but are not limited to these examples:

Proteins, hormones, enzymes, antibodies, DNA, portions of DNA strands, inorganic nutrients, aqueous salt solutions, RNA, nucleic acids, aptamers, antigens, lipids, oligopeptides, polypeptides, cofactors, and polysaccharides.

A single cell, groups of cells, living cells, multi-cell assemblies, pluripotent cells, stem cells, heart cells, lung cells, muscle cells neurons, and neural networks.

Living tissue, skin, hair-producing tissue, nail-producing tissue, and brain tissue.

DNA-coated particles, protein-coated particles, and RNA-coated particles.

Functional supporting media such as nutrients and other life supporting material.

Organic tagging compounds and inorganic tagging compounds. A tagging compound is a compound that allows for the detection of the deposited composite material 26. This can be done to verify the correct placement of the deposited composite material 26 and to verify that the biomaterial is still living or active.

When more than one composite materials 16 is used, one or more of them can comprise a transfer material comprising an electronic transfer material. The electronic transfer material is used to create electronic circuitry on the receiving substrate 18. The electronic transfer material can be independently selected from the group consisting of metal, dielectric, resist, semiconductor, and combinations thereof. These methods for creating circuitry are described in detail in U.S. Pat. No. 6,177,151. The circuitry can be designed to interact with a deposited composite material 26 that comprises biomaterial.

It is the presence of the matrix material that provides the advantages that the present invention has over methods such as laser induced forward transfer (LIFT). The matrix material is selected primarily according to two criteria: the matrix material must be compatible with the transfer material so that the matrix material and the transfer material can be combined into a mixture to form the composite material 16 on the support surface 32 of the laser-transparent support 15, and the matrix material must have the property of being desorbed from the laser-transparent support 15 when exposed to laser energy 14. When the composite material 16 is exposed to the laser energy 14, the matrix material may evaporate via electronic and vibrational excitation. The evaporated interfacial layers of matrix material then release the remaining composite material 16 so that the composite material 16 desorbs from the support surface 32 of the laser-transparent support 15 and moves toward the receiving substrate 18. The amount of matrix material that is used in the composite material 16 relative to the amount of the transfer material can be any amount sufficient to accomplish the purposes described above. Typically, the amount will vary according to the particular matrix material and transfer material.

Suitable matrix materials can comprise any of the following examples, but are not limited to these examples: glycerol, water, polymer, cell medium, cell nutrient, natural hydrogel, synthetic hydrogel, surfactant, antibiotic, antibody, antigen, protein, dimethylsulfoxide, water/dimethylsulfoxide mixture, agarose, saline solution, dielectric particles, metal particles, aqueous inorganic salt solution, nitrocellulose gel, sol gel, ceramic composite, DNA-coated particles, protein-coated particles, and RNA-coated particles.

An important property of the matrix material is its ability to maintain the biomaterial in a living or active state. Such matrix materials appropriate for various biomaterials are known in the art. Other factors that can be taken into account in selecting the optimum matrix material to go with a particular transfer material include the ability of the matrix material to form a colloidal or particulate suspension with the particular transfer material, the melting point, heat capacity, molecular size, chemical composition, spectral absorption characteristics and heat of vaporization of the matrix material (factors that affect the ability of the matrix material to desorb and lift the transfer material from the laser-transparent support 15) and the reactivity or nonreactivity of the matrix material towards the transfer material.

The matrix material may also serve other functions. For example, the matrix material may help prevent the transfer material from binding too tightly to the laser-transparent support 15. At the same time, the presence of the matrix material may aid in the construction of the composite material 16 on the laser-transparent support 15 by helping to hold the transfer material in place on the laser-transparent support 15, especially if the transfer material is a powder. This can sometimes be achieved by freezing the composite material 16 to the laser-transparent support 15 if the composite material 16 is a liquid at room temperature. The composite material 16 may be coated onto the support surface 32 of the laser-transparent support 15 and then the composite material 16 may be frozen to form a solid coating. The target substrate 17 may be kept frozen while the composite material 16 is being exposed to the laser energy 14 during the deposition process. The rest of the apparatus need not be kept frozen during the deposition process.

Freezing is appropriate when the matrix material comprises a water/glycerol solution or a water/dimethylsulfoxide solution. The freezing temperature for some composite materials 16 may be in the range from about −50° C. to about 100° C. The composite material 16 may also be held at the incubation temperature of the biomaterial to assist in keeping the biomaterial in its living or active state.

Another consideration is any special ability a particular matrix material may have to impart protection to a particular transfer material from damage during the lasing, desorption, and transfer to the receiving substrate 18. For example, a matrix material that absorbs laser energy 14 at the same wavelength as an important functional group on the transfer material may serve to protect the transfer material from damage from exposure to the laser energy 14. Alternatively, a matrix material may be used that absorbs at a wavelength in a spectral region substantially outside that of the transfer material. In this instance, the matrix material transforms laser energy into kinetic energy, and the kinetic energy is imparted to the transfer material. Examples of matrix materials include but are not limited to addition polymers (see below), condensation polymers (see below), photoresist polymers (see below), water, glycerol, dimethylsulfoxide, surfactant, aryl solvents, especially toluene, acetophenone and nicotinic acid, arene compounds (e.g. naphthalene, anthracene, phenanthrene), t-butylalcohol, halogenated organic solvent, hydrocarbons, ketones, alcohols, ethers, esters, carboxylic acids, phenols and phosphoric acid. It is also important sometimes to choose a matrix material that is a cushion for the transferred material, absorbing some of the impact energy, and limiting the damage to the transfer material.

The matrix material may also be a polymer that decomposes or "unzips" into volatile components when exposed to laser energy. The volatile decomposition products then act to propel or lift the transfer material off of the laser-transparent support 15. The polymeric matrix material acts as a propellant and at room temperature the propellant products are volatilized away while the transfer material is deposited as a thin film on the receiving substrate.

Unzipping mechanisms are typically catalyzed by a photon that is absorbed by the polymer and leads to chain cleavage, formation of a free radical (The free radical can be formed either by a thermally driven process or by a photochemical process) in the chain which then travels down the polymer chain leading to a chain unzipping that can produce the monomer species. The monomer, ejected at high kinetic energies, imparts some of this energy to the transfer material mixed with the polymer. One general controlling factor for depolymerization or unzipping of addition polymers is the ceiling temperature of the polymer. At the ceiling temperature, the rates of polymerization and depolymerization are equal. At temperatures above the ceiling temperature, depolymerization dominates polymerization. Laser radiation allows the high ceiling temperatures required for depolymerization to be reached between radiation pulses.

In general, polymeric propellants that are suitable candidates for consideration as matrix materials are taken from the class of polymers called addition polymers. As a subclass of addition polymers, the suitable candidate materials are typically sterically crowded and are generally thermally unstable. The general polymer classes that are of interest with known properties include poly(alkenes), poly(acrylics), poly(methacrylics), poly(vinyls), poly(vinylketones), poly(styrenes), poly (oxides), or polyethers. In general, addition polymers with alpha substituted structures consistently exhibit lower ceiling temperatures than their unsubstituted parent species and are strong candidate materials. Polymers from the class of materials called condensation polymers, as well as the class of materials called photoresist polymers, may also have some utility, especially if they decompose to volatile materials. The spectrum of candidate materials is wide and many polymer propellants can be used as the matrix material. Not all will be ideal in all characteristics. For example, repolymerization of a polymeric matrix material on the receiving substrate may be a problem with some materials. Other factors to be considered in the selection of the matrix material include the absorption of UV laser radiation, volatility of native propellant material, efficiency of the unzipping process, products of unzipping or decomposition and their volatilty/toxicity, kinetic energy imparted by the propellant, degree of repolymerization, inertness of binder material, inertness of unzipped or decomposed propellant, cost, availability, purity, and processability with the material of interest to be deposited.

Specific polymeric matrix materials include, but are not limited to, the following: polyacrylic acid-butyl ester, nitrocellulose, poly(methacrylic acid)-methyl ester (PMMA), poly(methacrylic acid)-n butyl ester (PBMA), poly(methacrylic acid)-t butyl ester (PtBMA), polytetrafluoroethylene (PTFE), polyperfluoropropylene, poly N-vinyl carbazole, poly(methyl isopropenyl ketone), poly alphamethyl styrene, polyacrylic acid, polyvinylacetate, polyvinylacetate with zinc bromide present, poly(oxymethylene), phenol-formaldehyde positive photoresist resins, and photobleachable aromatic dyes.

The matrix material may also contain components that assist in the bonding of the transfer material to the receiving substrate or that assist in the bonding of particles of the transfer material to each other after they are deposited on the receiving substrate.

The transfer material and the matrix material may be combined to form the composite material 16 on the support surface 32 of the laser-transparent support 15 in any manner that is sufficient to carry out the purpose of the invention. If the transfer material is soluble to some extent in the matrix material, the transfer material may be dissolved in the matrix material. Alternatively, if the transfer material is not soluble in a suitable solvent, the transfer material may be mixed with a matrix material to form a colloidal or particulate suspension or condensed phase. Still another alternative is to combine the matrix material and the transfer material with a solvent that volatilizes after the mixture is applied to the laser-transparent support 15. Still another alternative is to have a layer of matrix material, such as a hydrogel, between the transfer material and the laser-transparent support 15 without mixing the matrix material and the transfer material. The matrix material can also include soluble or insoluble dopants, that is, additional compounds or materials that one may wish to deposit onto the film.

The mixture of the transfer material and the matrix material may be applied to the support surface 32 of the laser-transparent support 15 by any method known in the art for creating uniform coatings on a surface, including, for example, by spin coating, ink jet deposition, jet vapor deposition, spin spray coating, aerosol spray deposition, electrophoretic deposition, pulsed laser deposition, matrix assisted pulsed laser evaporation, thermal evaporation, sol gel deposition, chemical vapor deposition, sedimentation and print screening. Typically, the mixture of the transfer material and the matrix material will be applied to the support surface 32 of the laser-transparent support 15 to form a composite material 16 that is between about 0.1 $\mu$m and about 100 $\mu$m in thickness. Preferably, the composite material 16 is greater than about 1 $\mu$m in thickness, and, most preferably, is between about 1 $\mu$m and about 20 $\mu$m in thickness. The thicker the composite material 16, the more of the transfer material can be transferred at one time, which is an advantage of the present invention over laser transfer methods that use thin films. On the other hand, a composite material 16 that is too thick will not desorb when exposed to the pulsed laser.

The embodiments described above can be combined in many ways, allowing for the deposition of complex multilayer, multi-component structures with a wide range of uses and applications. The examples demonstrate the capability of placing biomaterials (proteins, a cell, or group of cells) onto various surfaces in a computer-controlled fashion and on a 10's of micron scale. This ability allows the making of many structures and devices that require cells or other biomaterials to be placed in patterns or 3D shapes where there is microscopic structure. The following describes devices and their uses that could be made using the method of the invention. These descriptions of devices are not intended to limit the scope of the invention.

1) Engineered cellular or composite structures for growth, repair, replacement, or improvement of tissue: Tissue is comprised of precisely organized cells and biomolecules. Live tissue can be built from these components (using cells as bricks and biomolecules as mortar) by building complex cell structures in a computer-controlled manner. A specific goal would be to use this tissue to implant it in the body to heal or improve existing tissue.

2) Living organs: Organs are even more complicated tissue structures that perform specific life-sustaining functions in the body. They contain several types of cells and biomolecules but would be assembled the same as tissue discussed in 1).

3) Device to investigate inter- and intracellular signaling: There are several ways to investigate cell signaling including electronic detection, fluorescent probes, and gene or protein identification (cells use these molecules to communicate). The method allows the placement of cells on a detection platform. Specifically, to do electronic or protein identification, cells would be placed on an electronic circuit or in close proximity to a protein identification microarray.

4) Living device to control or divert the flow of fluid through microfluidic channels: Muscle and cardiac cells/tissue can be placed into microchannels. By placing the cells in a computer-controlled manner, a structure can be built that squeezes out fluid when all muscle cells are forced to contract at the same time using electrical stimulation. Likewise, a dam could be constructed from muscle tissue that could release or direct fluid down a microchannel depending on whether it was relaxed or contracted.

5) Living, miniature electrode: Neurons are essentially living electrodes that the brain and nervous system use to actuate functions in the body. Arrays and Microsystems of natural/living "electrodes" can be made by depositing subsystems of neurons.

6) Neural network: Same as 5) except the neurons are deposited in a connected network so that signals can pass from one area to another. The neural network can also mimic the transmission of impulses of the brain or nervous system by using computer-control and design to mimic structures found in the brain or nervous system. Communication lines that mimic the body's natural communications are also possible.

7) Device to investigate cell aging: Same as 3) except with the goal of detecting proteins or DNA corresponding to cell aging or death.

8) Bridge to connect a nerve synapse: This is the same as 5) and 6) but with the specific goal of repairing part of the natural nervous system inside the body.

9) Biofilm: Biofilms are organized, natural living structures that show signs of intelligence, i.e. advanced communication, organization, and function. They are made mainly from bacteria and excreted molecules, both of which can be deposited in patterns by the method of the invention. The idea would be to make a biofilm found in nature by constructing it from its basic components using computer controlled laser deposition of those materials.

10) Drug delivery system or coating: There are and will be new advanced molecules for coating and delivering drugs. Many of these classes of materials such as proteins or synthetic polymers can be deposited by the method of the invention. Films and structures of these materials can be made for improved drug coatings and delivery.

11) Implantable drug delivery system: A miniature biochip system, where one part contains a sensing or detecting element to detect a disease or medical condition, and another part contains a drug release function that is activated by the detection side, can be made by the method of the invention. The sensing element would contain an array of enzymes or antibodies sensitive to a variety of diseases or molecules characteristic of a disease. The drug delivery side would contain coated drug particles and a microfluidic injector to inject the drugs into the body.

12) Chemical or biological sensing device to sense chemicals or biomaterials: Bio- and chemical sensors rely upon active biomolecules or cells to sense the presence of a specific active molecule. The method of the invention can deposit these biomolecules and cells onto a detection platform (i.e. electronics, fluorescence, or magnetic) to make one of these devices.

13) Implantable, biocompatible sensor/signaler device: Like 12) except for the detection of non-diseased states such as a war-fighter monitor (fatigue, stress, wound, etc.) or a chemical or biological warfare agent.

Having described the invention, the following examples are given to illustrate specific applications of the invention. These specific examples are not intended to limit the scope of the invention described in this application.

EXAMPLE 1

Transfer of living *E. coli* bacteria from a frozen support— The transfer material was living *E. coli* cells. The matrix material was Luria-Bertani (LB) broth and kanamycin (50 µg/ml). The spot size was 0.09 cm$^2$ and the 193 nm energy density was 0.2 J/cm$^2$. The composite material 16 was frozen to the laser-transparent support 15. SEM micrographs showed that there was no damage to the transferred cells.

EXAMPLE 2

Transfer of living *E. coli* bacteria from a room temperature support—The transfer material was living *E. coli* cells. The matrix material was LB broth, agar, and kanamycin. The composite material 16 was coated on the laser-transparent support 15 and kept at room temperature. The same laser parameters as above resulted in successful transfer.

EXAMPLE 3

Transfer of living *E. coli* bacteria from a room temperature support—The transfer material was living GFP marked *E. coli* cells. The matrix material was LB broth, kanamycin, glycerin, and barium titanate nanoparticles. This transfer was performed with a different pulsed UV laser at 355 nm, a spot size of 65 microns, and an energy density of 1 J/cm$^2$. A SEM micrograph taken under UV light showed fluorescent activity in the transferred cells, proving that the cells were still living.

EXAMPLE 4

Transfer of living chinese hamster ovaries (CHO)—The transfer material was living Chinese hamster ovary cells. The matrix material was a hydrogel (Matrigel Matrix) layered below the living cells. The composite material 16 was kept at room temperature. This transfer was performed with 193 nm 30 ns laser pulses at an energy density of 150 mJ/cm$^2$. SEM micrographs showed that the cells were successfully transferred. Micrographs taken after three days after the transfer showed that the transferred cells had grown and multiplied on the receiving substrate 18.

EXAMPLE 5

Transfer of active horseradish peroxidase (HRP) from a frozen support—The transfer material was active HRP. The matrix material was PBS buffer. The concentration of HRP in the composite material 16 was 0.05 g HRP/g buffer. The composite material 16 was frozen to the laser-transparent support 15. The spot size was 0.09 cm$^2$ and the 193 nm energy density was 0.2 J/cm. Comparison of FTIR spectra of transferred HRP and spin-dried HRP confirmed that the transferred HRP was still active.

EXAMPLE 6

Transfer of active horseradish peroxidase (HRP) from a room temperature support—The transfer material was active HRP. The matrix material was PBS buffer and a 2 micron thick layer of polyurethane coated on the laser-transparent support 15. HRP/buffer solution dropped, spread, and dried on top of the polymer coating at an initial concentration of 0.05 g HRP/g buffer. The spot size was 0.09 cm$^2$, and the 193 nm energy density was 0.2 J/cm$^2$. A $H_2O_2$/DAB activity test showed that the transferred HRP was still active.

EXAMPLE 7

Transfer of living human osteoblasts from a room temperature support—The transfer material was living human osteoblasts. The matrix material was a hydrogel (Matrigel Matrix) layered below the living cells. This transfer was performed with 193 nm 30 ns laser pulses at an energy density of <20 mJ/cm$^2$. Green fluorescence after laser transfer and 20 hours of culture indicated live cells and near 100% viability.

EXAMPLE 8

Transfer of living mouse stem cells (pluripotent cells) from a room temperature support—The transfer material was living mouse stem cells. The matrix material was with a hydrogel (Matrigel Matrix) layered below the living cells. This transfer was performed with 193 nm 30 ns laser pulses at an energy density of <20 mJ/cm$^2$. Green fluorescence after laser transfer and 3 days of culture indicated live cells and near 100% viability.

We claim:

1. A method for laser deposition comprising the steps of;
providing one or more sources of laser energy that produce laser energy;
providing a receiving substrate;
   wherein the receiving substrate is positioned opposite the source of laser energy;
providing a target substrate;
   wherein the target substrate is positioned between the receiving substrate and the source of laser energy;
   wherein a gap exists between the receiving substrate and the target substrate;
   wherein the target substrate comprises a laser-transparent support and a composite material;
   wherein the laser-transparent support has a laser-facing surface facing the source of laser energy;
   wherein the laser-transparent support has a support surface facing the receiving substrate;
   wherein the composite material has a back surface in contact with the support surface;
   wherein the composite material has a front surface facing the receiving substrate;
   wherein the composite material comprises a mixture of a matrix material and a transfer material; and
   wherein the matrix material has the property of being desorbed from the laser-transparent support when exposed to the laser energy;

positioning the source of laser energy in a spaced relation to the target substrate so that the laser energy will strike the composite material at a defined target location;

positioning the receiving substrate in a spaced relation to the target substrate; and exposing the target substrate to the laser energy;

wherein the laser energy is directed through the laser-facing surface and through the laser-transparent support to strike the composite material at the support surface-back surface interface at the defined target location;

wherein the laser energy has sufficient energy to cause the desorption of the composite material from the support surface; and wherein the desorbed composite material is deposited at a defined receiving location on the receiving substrate to form a deposited composite material.

2. The method of claim 1, wherein the method is controlled by a computer.

3. The method of claim 1, wherein the steps are carried out at about room temperature; and wherein the steps are carried out at about atmospheric pressure.

4. The method of claim 1, wherein the steps are carried out under one or more controlled conditions selected from the group consisting of humidity, atmospheric composition, air pressure, temperature, sterility.

5. The method of claim 1, wherein the source of laser energy is a pulsed laser.

6. The method of claim 1, wherein the laser energy is focussed through an objective.

7. The method of claim 1, wherein the steps of positioning the source of laser energy and positioning the receiving substrate are achieved through the use of one or more positioning means selected from the group consisting of a laser positioning means, a target substrate positioning means, and a receiving substrate positioning means.

8. The method of claim 1, wherein the steps of positioning the source of laser energy, positioning the receiving substrate, and exposing the target substrate are repeated at successive defined target locations and successive defined receiving locations; and wherein the composite material is deposited in a two-dimensional pattern or a three-dimensional pattern of deposited composite material.

9. The method of claim 1, wherein the laser-transparent support comprises quartz or machine etched quartz.

10. The method of claim 1, wherein the laser-transparent support comprises a laser-transparent flexible polymer ribbon.

11. The method of claim 1, wherein the receiving substrate comprises a non-planar surface.

12. The method of claim 1, wherein the receiving substrate comprises one or more materials selected from the group consisting of chemically functionalized glass, polymer-coated glass, quartz, natural hydrogel, synthetic hydrogel, uncoated glass, nitrocellulose coated glass, silicon, glass, plastics, metals, and ceramics.

13. The method of claim 1, wherein the matrix material comprises one more materials selected from the group consisting of glycerol, water, polymer, cell medium, cell nutrient, natural hydrogel, synthetic hydrogel, surfactant, antibiotic, antibody, antigen, protein, dimethylsulfoxide, water/dimethylsulfoxide mixture, agarose, saline solution, dielectric particles, metal particles, aqueous inorganic salt solution, nitrocellulose gel, sol gel, ceramic composite, DNA-coated particles, protein-coated particles, and RNA-coated particles.

14. The method of claim 1, wherein the matrix material comprises a mixture of water and glycerol.

15. The method of claim 1, wherein the composite material is frozen to the laser-transparent support.

16. The method of claim 1, wherein the composite material is at a temperature of from about −50° C. to about 100° C.

17. The method of claim 1, wherein the deposited composite material is an engineered cellular or composite structures for growth, repair, replacement, or improvement of tissue.

18. The method of claim 1, wherein the deposited composite material is a living organ.

19. The method of claim 1, wherein the deposited composite material is a device to investigate inter- and intracellular signaling.

20. The method of claim 1, wherein the deposited composite material is a living device to control or divert the flow of fluid through microfluidic channels.

21. The method of claim 1, wherein the deposited composite material is a living, miniature electrode.

22. The method of claim 1, wherein the deposited composite material is a neural network.

23. The method of claim 1, wherein the deposited composite material is a device to investigate cell aging.

24. The method of claim 1, wherein the deposited composite material is a bridge to connect a nerve synapse.

25. The method of claim 1, wherein the deposited composite material is a biofilm.

26. The method of claim 1, wherein the deposited composite material is a drug delivery system or coating.

27. The method of claim 1, wherein the deposited composite material is an implantable drug delivery system.

28. The method of claim 1, wherein the deposited composite material is a chemical or biological sensing device to sense chemicals or biomaterials.

29. The method of claim 1, wherein the deposited composite material is an implantable, biocompatible sensor/signaler device.

30. The method of claim 1 comprising the following additional steps performed before the step of providing a target substrate:

positioning the receiving substrate in a spaced relation to the source of laser energy; and exposing the receiving substrate to the laser energy so that the laser energy machines away a defined machining location on the receiving substrate.

31. The method of claim 30, wherein the defined machining location comprises a via through the receiving substrate.

32. The method of claim 30, wherein the composite material is deposited into a defined machining location that has been previously machined away by the laser energy.

33. The method of claim 1 comprising the following additional steps after the step of exposing the target substrate:

removing the target substrate from its position between the source of laser energy and the receiving substrate;

positioning the receiving substrate in a spaced relation to the source of laser energy; and exposing the receiving substrate to the laser energy so that the laser energy machines away a defined machining location on the receiving substrate or on the deposited composite material.

34. The method of claim 33, wherein the defined machining location comprises a via through the receiving substrate.

35. The method of claim 1,
wherein the step of providing a target substrate is repeated one or more times using target substrates comprising different composite materials; and
wherein the different composite materials are deposited in respective patterns on the receiving substrate.

36. The method of claim 35, wherein the different composite materials comprise different transfer materials.

37. The method of claim 35,
wherein one or more composite materials comprise a matrix material and an electronic transfer material; and
wherein one or more electronic transfer materials are used to create electronic circuitry on the receiving substrate.

38. The method of claim 37, wherein the one or more electronic transfer materials are independently selected from the group consisting of metal, dielectric, resist, semiconductor, and combinations thereof.

39. The method of claim 1, wherein the receiving substrate comprises functionalization selected from the group consisting of covalent functionalization, physisorbed functionalization, and combinations thereof.

40. The method of claim 39, wherein the functionalization is selected from the group consisting of a living host, a living cell, a living cell culture, a non-living cell, a non-living group of cells, a living tissue, a chemically functionalized surface, and a biologically functionalized surface.

41. The method of claim 1, wherein the transfer material comprises a biomaterial.

42. The method of claim 41, wherein the biomaterial comprises one or more materials selected from the group consisting of proteins, hormones, enzymes, antibodies, DNA, portions of DNA strands, inorganic nutrients, aqueous salt solutions, RNA, nucleic acids, aptamers, antigens, lipids, oligopeptides, polypeptides, cofactors, and polysaccharides.

43. The method of claim 41, wherein the biomaterial comprises one or more materials selected from the group consisting of a single cell, groups of cells, living cells, multi-cell assemblies, pluripotent cells, stem cells, heart cells, lung cells, muscle cells neurons, and neural networks.

44. The method of claim 41, wherein the biomaterial comprises one or more materials selected from the group consisting of living tissue, skin, hair-producing tissue, nail-producing tissue, and brain tissue.

45. The method of claim 41, wherein the biomaterial comprises one or more materials selected from the group consisting of DNA-coated particles, protein-coated particles, and RNA-coated particles.

46. The method of claim 41, wherein the biomaterial comprises one or more functional supporting media selected from the group consisting of nutrients, and other life supporting material.

47. The method of claim 41, wherein the biomaterial comprises one or more tagging compounds selected from the group consisting of organic tagging compounds and inorganic tagging compounds.

48. The method of claim 41, wherein the composite material is at about the incubation temperature of the biomaterial.

49. The method of claim 41, wherein the biomaterial is living or active.

50. The method of claim 49, wherein the living or active biomaterial remains living or active on the receiving substrate.

* * * * *